US010222322B2

United States Patent
Ciobanu et al.

(10) Patent No.: US 10,222,322 B2
(45) Date of Patent: Mar. 5, 2019

(54) COLORIMETRIC ANALYZER WITH IMPROVED ERROR DETECTION

(71) Applicant: Rosemount Inc., Shakopee, MN (US)

(72) Inventors: Calin I. Ciobanu, Brea, CA (US); Hoang M. Nguyen, Irvine, CA (US); Jung S. Hwang, Newport Beach, CA (US); Jeffrey L. Lomibao, Corona, MN (US); Behzad Rezvani, Anaheim, CA (US)

(73) Assignee: Rosemount Inc., Shakopee, MN (US)

( * ) Notice: Subject to any disclaimer, the term of this patent is extended or adjusted under 35 U.S.C. 154(b) by 0 days.

(21) Appl. No.: 15/617,438

(22) Filed: Jun. 8, 2017

(65) Prior Publication Data

US 2018/0356335 A1    Dec. 13, 2018

(51) Int. Cl.
*G01N 21/31* (2006.01)
*G01N 21/25* (2006.01)

(52) U.S. Cl.
CPC ......... *G01N 21/251* (2013.01); *G01N 21/255* (2013.01); *G01N 21/31* (2013.01); *G01N 2201/127* (2013.01)

(58) Field of Classification Search
CPC .... G01N 21/251; G01N 21/255; G01N 21/31; G01N 21/127
USPC ........................................................ 356/402
See application file for complete search history.

(56) References Cited

U.S. PATENT DOCUMENTS

| 6,118,541 A * | 9/2000 | Mizzer ................. G01N 21/272 356/320 |
| 2014/0204382 A1* | 7/2014 | Christensen ........... G01N 21/39 356/402 |
| 2015/5099303 | 4/2016 | Butcher et al. |

OTHER PUBLICATIONS

First Office Action for Chinese Utility Model Patent Application No. 201721112501.4, dated Feb. 11, 2018, 4 pages. English translation included.
International Search Report and Written Opinion, dated Sep. 17, 2018, for International Patent Application No. PCT/US208/035056, 10 pages.
Rejection Decision, dated Aug. 1, 2018, for Chinese Utility Model Patent Application No. 201721112501.4, 5 pages including English translation.

* cited by examiner

*Primary Examiner* — Hina F Ayub
(74) *Attorney, Agent, or Firm* — Christopher R. Christenson; Kelly, Holt & Christenson, PLLC

(57) ABSTRACT

A colorimetric analyzer includes a reaction chamber configured to receive a sample and at least one reagent. A measurement cell is operably coupled to the reaction chamber. The colorimetric analyzer has an illumination source configured to emit illumination at a first wavelength during a first absorbance measurement and at a second wavelength during a second absorbance measurement. The colorimetric analyzer also includes an illumination detector spaced from the illumination source such that illumination from the illumination source passes through the measurement cell to the illumination detector. A controller is coupled to the illumination source and the illumination detector. The controller is configured to detect an obstruction of light between the illumination source and the illumination detector based on the first and the second absorbance measurements.

16 Claims, 3 Drawing Sheets

COLORIMETRIC ANALYZER WITH IMPROVED ERROR DETECTION

BACKGROUND

Online wet chemistry analyzers are used in a variety of industries to provide a continuous indication of an analyte in a process sample. This continuous indication can be provided locally by the analyzer and/or remotely to one or more suitable devices in order to provide control and/or monitoring of a chemical process.

One particular example of an online wet chemistry analyzer is an online automatic colorimetric analyzer. Such devices are configured to generate a reaction in the process sample that creates a visual indication relative to the process sample. This visual indication is measured by an optical sensor or light detector in order to provide an indication relative to the reaction. Colorimetric analysis is used in a variety of settings ranging from medical laboratories to industrial wastewater treatment facilities. Such analysis may be used with or without an enzymatic stage and is applicable to detecting both inorganic and organic compounds. Colorimetric techniques are known for detecting calcium, copper, creatine, iron, phosphate, cholesterol, glucose, urea, triglycerides, and silica.

One particular example of an automatic colorimetric analyzer is an online silica analyzer that employs a known reaction to render the silica in the process sample readily detectable. One example of such a reaction is known as the molybdenum blue method. In the molybdenum blue method, molybdate (usually in the form of potassium molybdate) is used to react with silica in the process sample in order to generate a compound suitable for colorimetric detection. In accordance with the molybdenum blue method, the silica content in water is measured based on the color of the silicomolybdic acid formed through the wet chemistry process. The molybdenum blue method can also be used for colorimetric qualitative analyses of phosphorous, arsenic, and germanium.

SUMMARY

A colorimetric analyzer includes a reaction chamber configured to receive a sample and at least one reagent. A measurement cell is operably coupled to the reaction chamber. The colorimetric analyzer has an illumination source configured to emit illumination at a first wavelength during a first absorbance measurement and at a second wavelength during a second absorbance measurement. The colorimetric analyzer also includes an illumination detector spaced from the illumination source such that illumination from the illumination source passes through the measurement cell to the illumination detector. A controller is coupled to the illumination source and the illumination detector. The controller is configured to detect an obstruction of light between the illumination source and the illumination detector based on the first and the second absorbance measurements.

DETAILED DESCRIPTION

Figure 1:
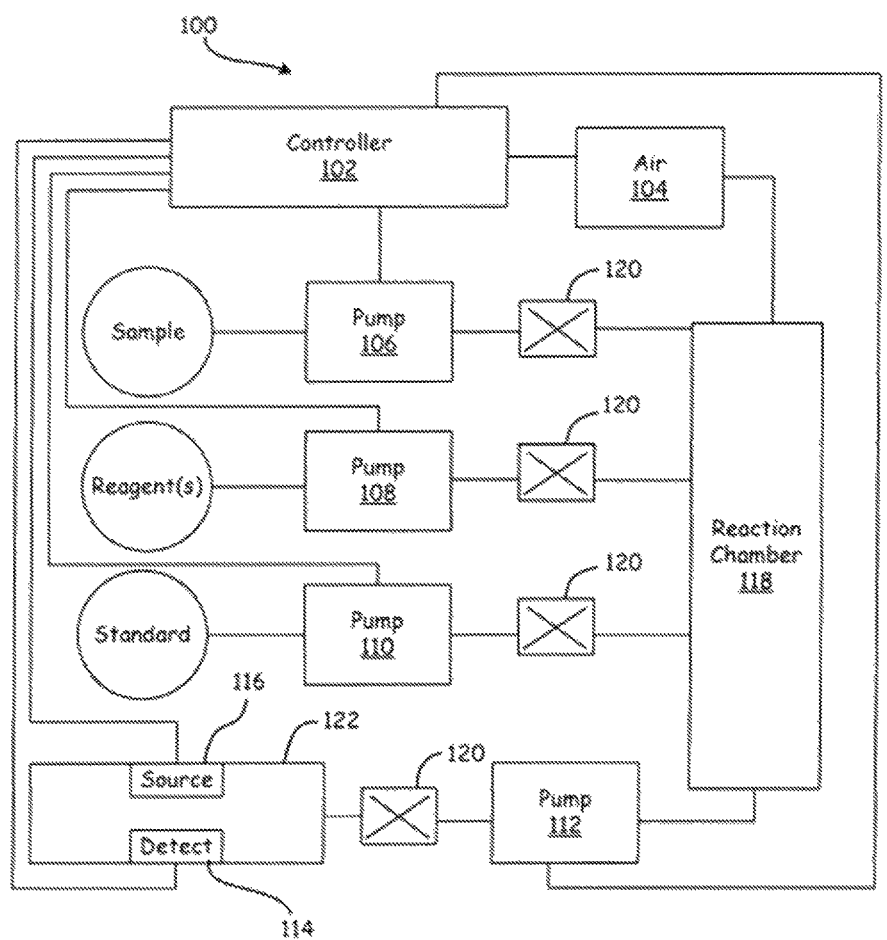
FIG. 1 is a diagrammatic view of an online silica analyzer with which embodiments of the present invention are particularly useful.

Colorimetric detection methods are available to measure a concentration of reactants, products or trace compounds of a reaction, for example, by measuring absorbance of a reaction mixture during a reaction process. A colorimetric analyzer can be used in any continuous process wherein reagents are mixed with a continuous stream of liquid to be tested. During operation, a liquid sample, that includes an analyte to be measured, is pumped or otherwise conveyed into a reaction chamber. Reagent(s) can then be provided into the reaction chamber, forming a complex with the analyte in the liquid sample allowing the analyte to be readily detectable. The mixture is then pumped or otherwise conveyed into a measurement cell and is subjected to colorimetric analysis. A concentration of the analyte can be calculated using a detected absorbance of the complex in accordance with Beer-Lambert's Law. Beer-Lambert's Law states that an analyte's absorbance can be measured as a logarithmic ratio of two measured light intensities, where $I_0$ represents the intensity of the light entering the sample and I represents the intensity of the light leaving the sample. An analyte's concentration may then be determined from the calculated absorbance value. The Beer-Lambert Law is expressed as follows, where $\varepsilon$ is molar absorptivity, l is a length of a solution the light passes through, and c is concentration:

$$A=\log(I_0/I)=\varepsilon lc \quad \text{(Equation 1)}$$

However, repeatability of absorbance values is necessary to accurately calculate a concentration of the analyte, since the concentration is based on the calculated absorbance values. To have repeatable absorbance values, the measurement cell needs to be filled completely each cycle so that illumination from the illumination source can completely traverse the mixture within the measurement cell. An issue arises when the mixture does not completely fill the measurement cell and a water/air interface is introduced into the measurement cell leading to an obstruction or at least partial obstruction of illumination within the measurement cell. In this circumstance, the intensities of light entering the cell, $I_0$, and leaving the cell, I, can be affected leading to inaccurate absorbance values, which, in turn, lead to inaccurate concentration readings. In accordance with an embodiment of the present invention, an improved colorimetric analyzer is provided that is can detect such an obstruction of illumination within a measurement cell.

While it is to be understood that the present disclosure is capable of being used in a variety of different colorimetric assays, for purposes of explanation only, embodiments of the invention will be described as they would be used to test for the presence of soluble silicates (silica). In power plants, the presence of such silicates is undesirable because of their tendency to coat the turbine blades.

During silica measurement using a colorimetric method, a chelating reagent is typically added to the sample solution first, forming a complex. In one example, this chelating agent is an acid solution of $Mo^{VI}$, for example ammonium molybdate. Then, a reducing reagent is added to reduce the complex which turns the solution blue. Examples of reducing reagents include ascorbic acid and/or ferrous ion. An absorbance measurement of the blue solution at 810 nm, for example, is then carried out. A concentration of silica is then calculated using the measured absorbance value.

FIG. 1 is a diagrammatic view of an online silica analyzer with which embodiments of the present invention are particularly useful. Analyzer 100 includes controller 102 that is coupled to air source 104 and pumps 106, 108, 110 and 112. Additionally, controller 102 is also coupled to illumination source 116 and illumination detector 114. Typically, each pump 106, 108, 110 and 112 is a peristaltic pump that employs peristaltic action to move its respective liquid. Cavity volumes are typically 2.5 mL for sample and standards (pumps 106 and 110) and 0.2 mL for reagents (pump 108). However, any suitable volumes can be used for the sample, standards, and reagents. In addition, a number of check valves 120 are provided in order to prevent backflow. When mixing of the sample/reagent/standards is desired, controller 102 engages air source 104 to pump a quantity of air into reaction chamber 118 to mix the contents therein. After a suitable time period, the mixed sample is pumped, using pump 112, to measurement cell 122. Once the mixed sample is provided within measurement cell 122, controller 102 engages illumination source 116 to direct measurement illumination through the mixed sample toward detector 114.

In one embodiment, illumination source 116 is able to generate illumination at multiple wavelengths. For example, controller 102 engages illumination source 116 to direct illumination having an infrared wavelength, 700 nanometers (nm)–1 millimeter (mm), toward detector 114. Subsequently, controller 102 can direct illumination having a visible wavelength, 400 nm-700 nm, toward detector 114. It is to be understood that illumination source 116 can direct illumination at a variety of wavelengths in accordance with an embodiment of the present invention. However, for silica, the measurement illumination will be substantially monochromatic having a wavelength of about 810 nm for the first measurement, and 670 nm for the second measurement. In accordance with known techniques, the illumination detected by detector 114 provides an indication of the analyte in the sample. Once the measurement is complete, repeated flushes with fresh sample remove the treated sample from the measurement and reaction cells 122 and 118, respectively.

If measurement cell 122 is not completely filled with a mixed sample, a water/air interface can be introduced leading to an illumination obstruction within measurement cell 122. In turn, this can lead to an inaccurate reading. In accordance with an embodiment of the present invention, an improved colorimetric analyzer is provided capable of detecting and removing erroneous measurements stemming from the obstruction.

Figure 2:
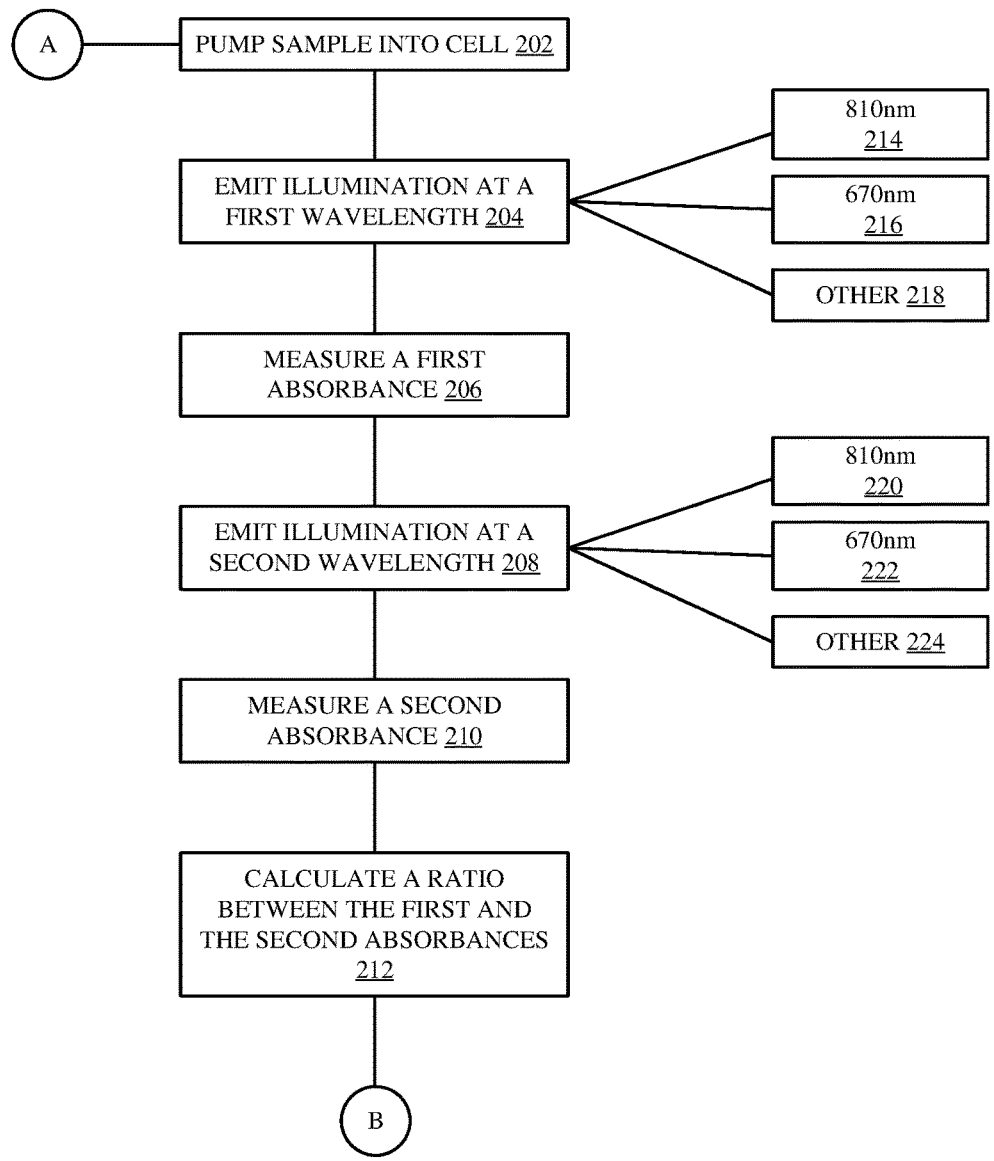
FIG. 2 is a flow diagram of a method of calculating a sensitivity ratio in accordance with an embodiment of the present invention.

FIG. 2 is a flow diagram of a method of calculating a sensitivity ratio in accordance with an embodiment of the present invention. A calculated sensitivity ratio can be used to determine whether an obstruction is present within measurement cell 122. It is to be understood that the determination of an obstruction within measurement cell may be determined by controller 102 or any other suitable device coupled to analyzer 100.

Method 200 begins at block 202 where a mixed sample is pumped into a measurement cell. Method 200 then turns to block 204 where an illumination source emits illumination at a first wavelength based on the analyte to be measured within the sample. For example, for a silica based sample, two absorbance peaks are observed at 670 nm and 810 nm. Therefore, the first wavelength may be 810 nm, as indicated in block 214. Alternatively, the first wavelength may be 670 nm, as indicated in block 216. Alternatively, for a non-silica based sample, it is to be understood that other wavelengths may be used in accordance with an embodiment of the present invention, as indicated in block 218.

A first absorbance is then measured, as indicated in block 206. Method 200 then proceeds to block 208 where illumination source 116 emits illumination at a second wavelength, different than the first wavelength, through the sample. For example, if the first wavelength is 670 nm, the second wavelength may be 810 nm, as indicated in block 220. Alternatively, if the first wavelength is 810 nm, the second wavelength may be 670 nm, as indicated in block 222. However, for non-silica based samples, other wavelengths may be used in accordance with embodiments of the present invention, as indicated in block 224.

A second absorbance is then measured as indicated in block 210. Subsequently, a sensitivity ratio is calculated between the first absorbance value and the second absorbance value as indicated in block 212. Once the sensitivity ratio is calculated, it is used to determine whether an obstruction is present as will be discussed in FIG. 3.

Figure 3:
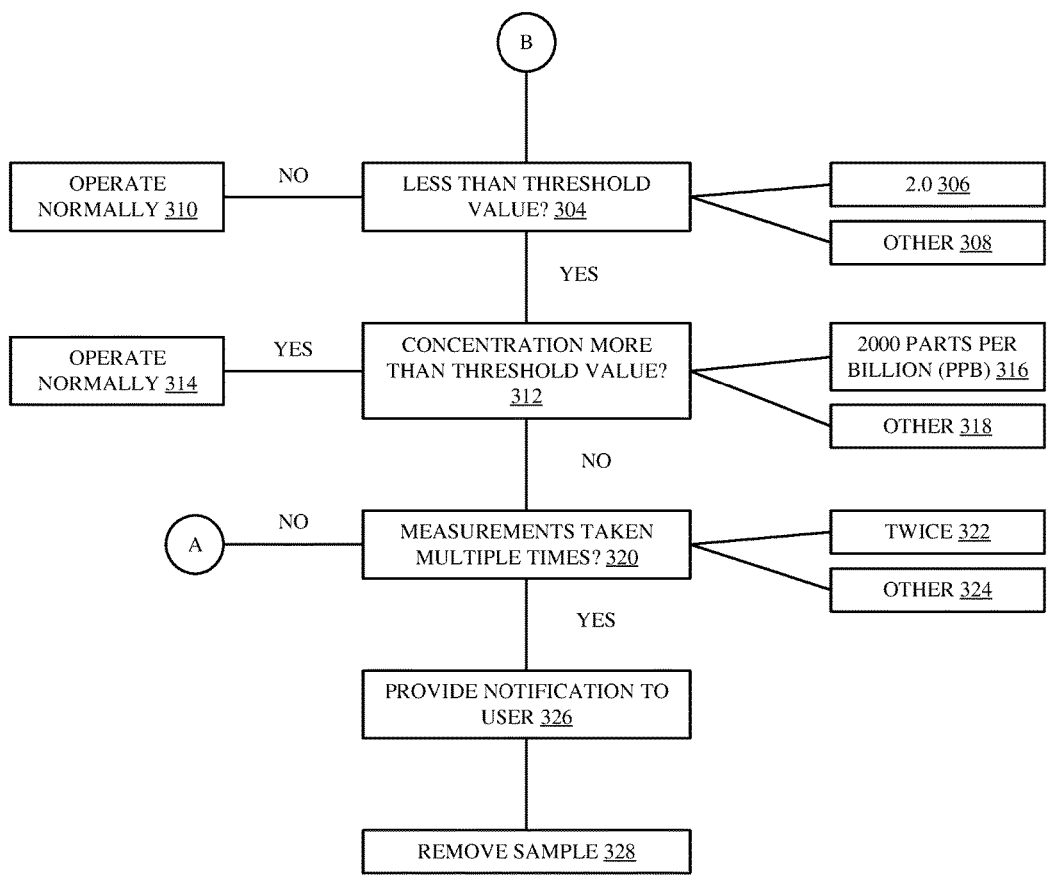
FIG. 3 is a flow diagram of detecting an obstruction of light in a colorimetric analyzer in accordance with an embodiment of the present invention.

FIG. 3 is a flow diagram of detecting an obstruction of light in a colorimetric analyzer in accordance with an embodiment of the present invention. Method 302 begins at block 304 where a determination is made whether a calculated sensitivity ratio is less than a threshold value. For a silica based sample, one preferred threshold value is 2.0, as indicated in block 306. However, for non-silica based samples, it is expressly contemplated that other threshold values may be used in accordance with embodiments of the present invention, as indicated in block 308.

If it is determined that the sensitivity ratio is greater than the threshold value, method 302 passes to block 310 where the colorimetric analyzer operates normally. If it is determined that the sensitivity ratio is less than the threshold value, method 302 passes to block 312 where a concentration value is compared to a concentration threshold value. In one embodiment, the concentration value is extrapolated based on either the first or the second absorbance values used to calculate the sensitivity ratio, as described in FIG. 2. For example, the concentration value is determined based on the measured absorbance, at 810 nm, used to calculate the sensitivity ratio. For a silica based sample, the concentration threshold includes a numerical value of 2000 parts per billion (ppb), as indicated in block 316. However, for non-silica based samples, it is expressly contemplated that other concentration thresholds may be used, as indicated in block 318. In one embodiment, both the threshold value and the concentration threshold value are stored within a non-volatile memory within a controller of the colorimetric analyzer.

If it is determined that the concentration value, corresponding to either the first or the second absorbance, is greater than the concentration threshold value, method 302 passes to block 314, where the colorimetric analyzer, or online silica analyzer in one embodiment, operates normally. However, if the concentration value is less than the concentration threshold value, method 302 passes to block 320.

In accordance with an embodiment of the present invention, if an obstruction is present within a measurement cell, the intensities of light entering and leaving the mixed sample will change, leading to a change in absorbance, and, subsequently, a change in a calculated sensitivity ratio. By comparing a calculated sensitivity ratio for a given sample to a predefined threshold value, and a calculated concentration value to a concentration threshold value, a presence of an obstruction can be determined.

In order to verify that an obstruction is present, a determination is made in block 320 as to the number of times an obstruction of light is detected. This may include determining a number of times that a sensitivity ratio was calculated and compared to a threshold value, and a concentration value was calculated and compared to a concentration threshold value, for a mixed sample. In one example, a determination may indicate that the process was carried out a total of two times, as indicated in block 322, or any other number of times, as indicated in block 324, indicating the presence or absence of an obstruction of light. If a determination is made that the process was only carried out a single time, the method returns to block 202, where a sample is pumped into a measurement cell. Upon returning to block 320, a determination can be made that the process was carried out multiple times for the mixed sample. Method 302 may then proceed to block 326 where a notification is provided to a user indicating an obstruction is present within a measurement cell, allowing the erroneous measurements to be disregarded. The mixed sample may then be removed from the measurement cell, as indicated in block 328.

Although the present invention has been described with reference to preferred embodiments, workers skilled in the art will recognize that changes may be made in form and detail without departing from the spirit and scope of the invention. Moreover, while embodiments of the present invention have generally been described with respect to a silica analyzer, embodiments are practicable with any colorimetric analyzer where colorimetric reagents have inherent interference in colorimetric detection and are not affected by the chemistry.

What is claimed is:

1. A colorimetric analyzer comprising:
   a reaction chamber configured to receive a sample and at least one reagent;
   a measurement cell operably coupled to the reaction chamber;
   an illumination source configured to emit illumination at a first wavelength during a first absorbance measurement and at a second wavelength during a second absorbance measurement;
   an illumination detector spaced from the illumination source such that illumination from the illumination source passes through the measurement cell to the illumination detector; and
   a controller coupled to the illumination source and the illumination detector, the controller being configured to detect an obstruction of light between the illumination source and the illumination detector based on the first and the second absorbance measurements and a comparison of a concentration value of the sample to a concentration threshold value.

2. The colorimetric analyzer of claim 1, wherein the obstruction of light is a water/air interface within the measurement cell.

3. The colorimetric analyzer of claim 1, wherein the colorimetric analyzer is an online silica analyzer.

4. The colorimetric analyzer of claim 3, wherein the first wavelength is 810 nm and the second wavelength is 670 nm.

5. The colorimetric analyzer of claim 3, wherein the ratio threshold value comprises a numerical value of 2.0.

6. The colorimetric analyzer of claim 3, wherein the concentration threshold value comprises a numerical value of 2000 parts per billion.

7. The colorimetric analyzer of claim 1, wherein the controller is further configured to, upon detecting the obstruction of light, provide a user indication of the obstruction of light.

8. The colorimetric analyzer of claim 1, wherein the obstruction of light is detected based on a calculated ratio between the first absorbance measurement and the second absorbance measurement.

9. The colorimetric analyzer of claim 8, wherein the calculated ratio is configured to be compared to a ratio threshold value particular to the sample.

10. The colorimetric analyzer of claim 1, wherein the controller is further configured to repeat, based on the concentration value, obtaining a first subsequent absorbance measurement and a second subsequent absorbance measurement and calculating a ratio between the first subsequent absorbance measurement and the second subsequent absorbance measurement.

11. A method of detecting an obstruction of light between an illumination source and an illumination detector of a colorimetric analyzer, comprising:
    obtaining a process sample having an analyte;
    reacting the analyte to provide a colorimetrically-detectable compound;
    measuring a first absorbance of the colorimetrically-detectable compound at an illumination having a first wavelength;
    measuring a second absorbance of the colorimetrically-detectable compound at an illumination having a second wavelength different than the first wavelength;
    calculating a ratio between the first absorbance and the second absorbance of the compound;
    comparing the calculated ratio to a threshold value;
    based on the comparison of the calculated ratio to the threshold value, comparing a concentration value to a concentration threshold value; and
    based on the calculated ratio and the comparison of the concentration value to the concentration threshold value, discarding the process sample and repeating the steps of obtaining a process sample, reacting an analyte, measuring a first and second absorbance, calculating a ratio, comparing the ratio and comparing a concentration value.

12. The method of claim 11, wherein the colorimetric analyzer measures one of the first and second absorbances before measuring the other of the first and second absorbances.

13. The method of claim 12, wherein the first wavelength is 810 nm and the second wavelength is 670 nm.

14. The method of claim 13, wherein the ratio threshold value comprises a numerical value of 2.0.

15. The method of claim 11, wherein the concentration threshold value comprises a numerical value of 2000 parts per billion.

16. The method of claim 11, and further comprising providing a notification of obstruction of light to a user based on the calculated ratio and the comparison of the concentration value to the concentration threshold value.

* * * * *